United States Patent

Huth et al.

[11] Patent Number: 5,750,525
[45] Date of Patent: May 12, 1998

[54] QUINOXALINEDIONE DERIVATIVES, THEIR PRODUCTION AND USE IN PHARMACEUTICAL AGENTS

[75] Inventors: Andreas Huth; Lechoslaw Turski, both of Berlin, Germany

[73] Assignee: Schering Aktiengesellschaft, Berlin, Germany

[21] Appl. No.: 537,839

[22] PCT Filed: Apr. 28, 1994

[86] PCT No.: PCT/DE94/00493

§ 371 Date: Mar. 8, 1996

§ 102(e) Date: Mar. 8, 1996

[87] PCT Pub. No.: WO94/25469

PCT Pub. Date: Nov. 10, 1994

[30] Foreign Application Priority Data

Apr. 28, 1993 [DE] Germany ............... 43 14 591.4
Dec. 21, 1993 [DE] Germany ............... 43 44 486.5

[51] Int. Cl.$^6$ .............. A61K 31/495; C07D 413/00; C07D 417/00; C07D 241/36

[52] U.S. Cl. .............. 514/249; 514/212; 514/228.2; 514/234.8; 540/599; 544/62; 544/116; 544/119; 544/232; 544/238; 544/243; 544/295; 544/337; 544/354

[58] Field of Search ............... 540/599; 544/62, 544/116, 119, 232, 238, 243, 295, 337, 354; 514/212, 228.2, 234.8, 249

[56] References Cited

U.S. PATENT DOCUMENTS

| | | | |
|---|---|---|---|
| 5,026,704 | 6/1991 | Honore et al. | 514/250 |
| 5,075,304 | 12/1991 | Hansen et al. | 514/233.2 |
| 5,166,155 | 11/1992 | Jorgensen et al. | 514/249 |
| 5,283,244 | 2/1994 | Sakamoto et al. | 514/249 |
| 5,514,680 | 5/1996 | Weber et al. | 514/249 |

FOREIGN PATENT DOCUMENTS

| | | |
|---|---|---|
| 315 959 | 5/1989 | European Pat. Off. . |
| 344 943 | 12/1989 | European Pat. Off. . |
| 556 393 | 8/1993 | European Pat. Off. . |
| WO 91/13878 | 9/1991 | WIPO . |
| WO 92/07847 | 5/1992 | WIPO . |
| WO 93/08173 | 4/1993 | WIPO . |
| WO 94/00124 | 1/1994 | WIPO . |

OTHER PUBLICATIONS

Lumma et al., Piperazinylquinoxalines with Central Serotoninmimetic Activity, Journal of Medicinal Chemistry, vol. 24, No. 1, pp. 93-101, 1981.

*Primary Examiner*—Matthew V. Grumbling
*Assistant Examiner*—Brenda Coleman
*Attorney, Agent, or Firm*—Millen, White, Zelano, & Branigan, P.C.

[57] ABSTRACT

Compounds of formula I are described

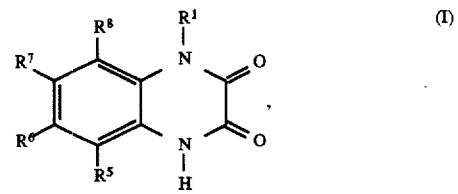

in which $R^1$, $R^5$, $R^6$, $R^7$ and $R^8$ have the meanings mentioned in the application as well as their production and use in pharmaceutical agents.

24 Claims, No Drawings

QUINOXALINEDIONE DERIVATIVES, THEIR PRODUCTION AND USE IN PHARMACEUTICAL AGENTS

This application was filed under 35 U.S.C. §371 from PCT/DE94/00493, filed Apr. 28, 1994.

The invention relates to quinoxalinedione derivatives, their production and use in pharmaceutical agents.

It is known that quinoxaline derivatives have an affinity to the quisqualate receptors and, because of the affinity, are suitable as pharmaceutical agents for the treatment of diseases of the central nervous system.

The compounds according to the invention have formula I

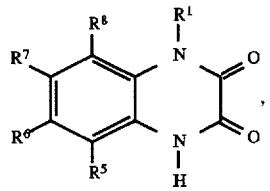

in which $R^1$ means —$(CH_2)_n$—$CR^2H$—$(CH_2)_m$—Z and $R^5$, $R^6$, $R^7$ and $R^8$ are the same or different and mean hydrogen, $C_{1-6}$ alkyl, $CF_3$, nitro, halogen, $NR^9R^{10}$, cyano, $SO_pR^{11}$, $SO_2NR^{12}R^{13}$, $SO_3H$, $SO_3C_{1-6}$ alkyl or $OR^{14}$ and $R^2$ means hydrogen or —$(CH_2)_q$, —$R^3$, $R^3$ means hydrogen, hydroxy, $C_{1-6}$ alkoxy or $NR^{15}R^{16}$, n, m and q each mean 0, 1, 2 or 3, Z means POXY, OPOXY, $OR^{17}$, $NR^{18}R^{19}$, NH—$COR^{20}$, NH—$SO_2R^{21}$, $SO_2R^{22}$, $CO_2R^{23}$, halogen, cyano or tetrazole $R^{11}$ means H, $C_{1-6}$ alkyl, phenyl p means 0, 1 or 2, $R^{12}$, $R^{13}$, $R^{17}$ and $R^{23}$ mean hydrogen or $C_{1-4}$ alkyl, $R^{14}$ means H or $C_{1-6}$ alkyl optionally substituted one to three times with halogen, $R^{20}$ and $R^{21}$ mean $C_{1-6}$ alkyl, phenyl or hetaryl optionally substituted with halogen, $R^{22}$ means hydroxy, $C_{1-6}$ alkoxy or $NR^{24}R^{25}$, X and Y are the same or different and mean hydroxy, $C_{1-6}$ alkoxy, $C_{1-4}$ alkyl or $NR^{18}R^{19}$, $R^9$ and $R^{10}$ are the same or different and mean hydrogen, CO—$C_{1-6}$ alkyl, phenyl or $C_{1-6}$ alkyl that can optionally be substituted with $C_{1-4}$ alkoxy or an amino group optionally mono- or disubstituted with $C_{1-4}$ alkyl, or together with the nitrogen atom form a 5- to 7-membered saturated heterocycle that can contain another N, S or O atom and can be substituted or form an unsaturated 5-membered heterocycle that can contain 1–3 N atoms and can be substituted, $R^{15}$ and $R^{16}$, $R^{18}$ and $R^{19}$ are the same or different and mean hydrogen, $C_{1-4}$ alkyl, phenyl or together with the nitrogen atom form a 5- to 7-membered saturated heterocycle that can contain another oxygen, sulfur or nitrogen atom and can be substituted or form an unsaturated 5-membered heterocycle that can contain 1–3 N atoms and can be substituted, $R^{24}$ and $R^{25}$ are the same or different and mean hydrogen, $C_{1-4}$ alkyl or together with the nitrogen atom form a saturated 5- to 7-membered heterocycle that can contain another oxygen, sulfur or nitrogen atom, as well as their isomers or salts, and, if $R^2$ is hydrogen and Z is POXY or $CO_2R^{23}$, $R^5$–$R^8$ do not mean hydrogen and if $R^2$ means hydrogen, Z means POXY or $CO_2R^{23}$ and $R^5$, $R^6$, $R^7$ or $R^8$ mean $CF_3$, $NO_2$, halogen, $NH_2$ or methyl, disubstituted compounds of formula I are present and if $R^1$ is methanephosphonic acid and $R^6$ is cyano or substituted imidazole, $R^5$, $R^7$ and $R^8$ cannot be hydrogen at the same time, and if $R^1$ is methanephosphonic acid and $R^6$ is $CF_3$, $NO_2$ and $R^7$ is imidazole, $R^5$ and $R^8$ cannot be hydrogen at the same time and if $R^1$ means —$CH_2$—COOH and $R^5$ and $R^8$ mean hydrogen, $R^6$ and $R^7$ do not mean halogen or methyl at the same time.

The compounds of general formula I also contain the possible tautomeric forms and comprise the E or Z isomers or, if a chiral center is present, the racemates or enantiomers.

The substituents are preferably in 6- and/or 7-position.

Alkyl is to be understood to mean respectively a straight-chain or branched alkyl radical, such as, for example, methyl, ethyl, propyl, isopropyl, butyl, isobutyl, sec-butyl, pentyl, isopentyl, hexyl, and $C_{1-4}$ alkyl radicals are preferred.

Halogen is to be understood to mean respectively fluorine, chlorine, bromine and iodine, especially fluorine, chlorine and bromine.

If $R^9$ and $R^{10}$, $R^{15}$ and $R^{16}$, $R^{18}$ and $R^{19}$, $R^{24}$ and $R^{25}$ together with the nitrogen atom form a saturated heterocycle, then, for example, piperidine, pyrrolidine, morpholine, thiomorpholine, hexahydroazepine or piperazine are meant. The heterocycle can be substituted one to three times with $C_{1-4}$ alkyl or aryl, such as phenyl. For example, N-methyl-piperazine, 2,6-dimethylmorpholine or phenylpiperazine can be mentioned.

If $R^9$ and $R^{10}$, $R^{15}$ and $R^{16}$, $R^{18}$ and $R^{19}$, together with the nitrogen atom, form an unsaturated heterocycle, then, for example, imidazole, pyrazole, pyrrole and triazole can be mentioned, which can be substituted once to twice with cyano, $C_{1-4}$ alkyl, phenyl or $CO_2C_{1-6}$ alkyl.

If an acid function is contained, the physiologically compatible salts of organic and inorganic bases are suitable as salts, such as, for example, the readily soluble alkali and alkaline-earth salts, as well as N-methyl-glucamine, dimethyl-glucamine, ethyl-glucamine, lysine, 1,6-hexadiamine, ethanolamine, glucosamine, sarcosine, serinol, tris-hydroxy-methyl-amino-methane, aminopropanediol, Sovak base, 1-amino-2,3,4-butanetriol.

If a basic function is contained, the physiologically compatible salts of organic and inorganic acids are suitable, such as HCl, $H_2SO_4$, phosphoric acid, citric acid, tartaric acid, etc.

As hetaryl radical $R^{20}$ and $R^{21}$, 6-ring heteroaromatic substances, such as pyridine, pyrazine, pyrimidine and pyridazine, are suitable.

Compounds with Z=-POXY, -$OR^{17}$, —$CO_2R^{23}$, -$NR^{18}R^{19}$, $SO_3H$ or tetrazole, which are substituted in 5-, 6-, 7- and/or 8-position with $C_{1-6}$ alkyl, $CF_3$, nitro, halogen, $SO_pR^{11}$, $SO_2NR^{12}R^{13}$ or $NR^9R^{10}$, are preferred.

Especially preferred are phosphonic acid and carboxylic acid derivatives, which can be substituted once to twice. Especially preferred are phosphonic acid derivatives that are substituted twice in 5-to 8-position. Preferred substituents $R^5$–$R^8$ are especially $NR^9R^{10}$ and $CF_3$.

The compounds of formula I as well as their physiologically compatible salts can be used as pharmaceutical agents because of their affinity for the AMPA receptors. Because of their action profile, the compounds according to the invention are suitable for the treatment of diseases that are caused by hyperactivity of excitatory amino acids, such as, for example, glutamate or aspartate. Since the new compounds act as antagonists of excitatory amino acids and show a high specific affinity for the AMPA receptors, in which they displace the radioactively labeled specific agonist (RS)α-amino-3-hydroxy-5-methyl-4-isoxazolpropionate (AMPA) from the AMPA receptors, they are especially suitable for the treatment of those diseases that are affected by the receptors of excitatory amino acids, especially the AMPA receptor.

According to the invention, the compounds can be used for the treatment of neurological and psychiatric disorders that are triggered by the overstimulation of the AMPA receptor. The neurological diseases that can be treated functionally and preventatively include neurodegenerative disorders, for example, such as Parkinson's disease, Alzheimer's disease, Huntington chorea, amyotrophic lateral sclerosis and olivopontocerebellar degeneration. According to the invention, the compounds can be used for the prevention of postischemic cell destruction, cell destruction after cerebral trauma, in a stroke, hypoxia, anoxia and hypoglycemia and for treatment of senile dementia, multiinfarct dementia as well as epilepsy and muscle spasms. The psychiatric diseases include anxiety conditions, schizophrenia, migraine, conditions of pain, as well as the treatment of sleep disorders and the withdrawal symptoms after drug abuse, such as in alcohol, cocaine, benzodiazepine or opiate withdrawal.

For use of the compounds according to the invention as pharmaceutical agents, they are put in the form of a pharmaceutical preparation, that, besides the active ingredient for enteral or parenteral administration, contains suitable pharmaceutical, organic or inorganic inert vehicles, such as, for example, water, gelatin, gum arabic, lactose, starch, magnesium stearate, talc, vegetable oils, polyalkyleneglycols, etc. The pharmaceutical preparations can be in solid form, for example, as tablets, coated tablets, suppositories, capsules or in liquid form, for example, as solutions, suspensions or emulsions. Moreover, they optionally contain auxiliary agents, such as preservatives, stabilizers, wetting agents or emulsifiers, salts for changing the osmotic pressure or buffers.

Especially suitable for parenteral use are injection solutions or suspensions, in particular aqueous solutions of the active compounds in polyhydroxy-ethoxylated castor oil.

Surface-active auxiliary agents, such as salts of bile acids or animal or vegetable phospholipids, but also their mixtures as well as liposomes or their components can also be used as vehicle systems.

Especially suitable for oral use are tablets, coated tablets or capsules with talc and/or hydrocarbon vehicles or binders, such as, for example, lactose, corn or potato starch. The use can even take place in liquid form, such as, for example, as juice to which a sweetener is optionally added.

The dosage of the active ingredients can vary depending on method of administration, age and weight of the patient, type and severity of the disease to be treated and similar factors. The daily dose is 0.5–1000 mg, preferably 50–200 mg, and the dose can be administered as a once-a-day dose or subdivided into 2 or more daily doses.

The production of the compounds according to the invention takes place according to methods known in the art. For example, compounds of formula I are achieved in that a) a compound of formula II

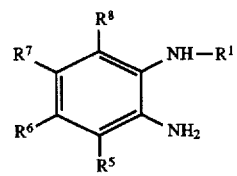

in which $R^1$ to $R^8$ have the above-mentioned meaning, is cyclized with oxalic acid or reactive oxalic acid derivatives or b) a compound of formula III

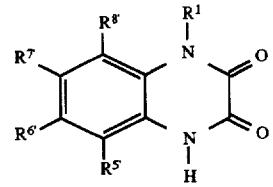

in which $R^1$ has the above-mentioned meaning and one of the substituents $R^{5'}$, $R^{6'}$, $R^{7'}$ or $R^{8'}$ represents a leaving group, is nucleophilically substituted and then optionally the ester group is saponified or the acid group is esterified or amidated or the nitro group is reduced to the amino group or the amino group is alkylated or acylated or the amino group is exchanged for halogen or cyano or a nitro group or halogen is introduced or an ether cleavage is performed or the alcohol is converted into a halide or this halogen is nucleophilically substituted or a nitrile is converted into the tetrazole or the isomers are separated or the salts are formed.

The cyclization to compounds of formula I takes place single-stage with oxalic acid in a known way in an acid environment or single-stage with a reactive oxalic acid derivative or else two-stage. Regarded as preferable is the two-stage process in which the diamine is reacted with an oxalic derivative such as oxalic ester semi-chloride or reactive oxalic acid imidazolide derivatives in polar solvents, such as cyclic or acyclic ethers or halogenated hydrocarbons, for example, tetrahydrofuran, diethyl ether or methylene chloride in the presence of a base such as organic amines, for example, triethylamine, pyridine, Hünig base or dimethylaminopyridine. The subsequent cyclization can be performed basic or else acidic, but preferably in an acid environment, and alcohol can be added to the reaction mixture as solubilizer.

Alkali hydrides such as NaH, that are used in inert solvents such as hydrocarbons or ethers, also represent suitable bases for the two-stage process.

As leaving groups in process variant b), as well as in the production of starting compounds of formula II, halogens such as fluorine, chlorine, bromine, iodine or o-mesylate, o-tosylate, o-triflate or o-nonaflate are suitable. The nucleophilic substitution is performed according to methods known in the literature in the presence of a base and is fostered by an activating electron-attracting group, such as, e.g., nitro, cyano, trifluoromethyl, preferably in o-position.

As nucleophiles, for example, primary and secondary amines, N-containing unsaturated or saturated heterocycles, cyanide, alcoholates, thiolate, i.a., are suitable. The reaction can be performed in polar solvents such as alcohols, halogenated hydrocarbons, dimethylacetamide, acetonitrile or water or without solvents. As bases, inorganic bases, such as alkali or alkaline-earth hydroxides or carbonates, or organic bases, such as cyclic, acyclic and aromatic amines, such as DBU, Hünig base, pyridine or dimethylaminopyridine, are suitable. In the case of amines, the nucleophile itself is used in excess as base, and optionally it is possible to work without further solvent. In the case of amine having too low a boiling point, the reaction can optionally be performed under pressure in an autoclave.

The optionally subsequent saponification of an ester group can take place in a basic or preferably acid manner, by hydrolyzing the reaction mixture at a higher temperature up to the boiling temperature in the presence of acids, such as highly concentrated aqueous hydrochloric acid optionally in solvents, such as, for example, trifluoroacetic acid or alcohols. Phosphonic acid esters are preferably hydrolyzed by heating in highly concentrated aqueous acids, such as, for example, concentrated hydrochloric acid optionally with addition of an alcohol or by treatment with a trimethylsilyl halide in inert solvents, such as, e.g., acetonitrile and subsequent treatment with water.

The esterification of the carboxylic acid or phosphonic acid takes place in a way known in the art with the corresponding alcohol by acid catalysis or in the presence of an activated acid derivative. As activated acid derivatives, for example, acid chloride, acid imidazolide or acid anhydride are suitable. In the phosphonic acids, the esterification can be achieved by reaction with orthoesters optionally by addition of catalysts such as p-toluene sulfonic acid.

The amidation takes place on the free acids or on their reactive derivatives, such as, for example, acid chlorides, mixed anhydrides, imidazolides or azides, by reaction with the corresponding amines at room temperature.

The reduction of the nitro group to an amino group takes place catalytically in polar solvents at room temperature or a higher temperature. As catalysts, metals such as Raney nickel or noble metal catalysts such as palladium or platinum, optionally on vehicles, are suitable. Instead of hydrogen, ammonium formate can also be used in a known way. Reducing agents such as tin(II)chloride or titanium(III) chloride can be used just as complex metal hydrides possibly in the presence of heavy metal salts. Iron is also usable as a reducing agent. The reaction is then performed in the presence of an acid, such as, e.g., acetic acid or ammonium chloride, optionally by addition of a solvent such as water. It can be advantageous to introduce the ester group before the reduction. In the presence of several nitro groups in the molecule, the desired nitro group in ortho position can also be selectively reduced with $Na_2S$ in the usual way.

If an alkylation of an amino group is desired, then alkylation can be performed according to usual methods, for example, with alkyl halides or according to the Mitsonubo variant by reaction with an alcohol in the presence of triphenylphosphine and azodicarboxylic acid ester or the amine is subjected to a reductive amination with aldehydes or ketones optionally in succession with two different carbonyl compounds, in which mixed derivatives are obtained (for literature, e.g., Verardo et al. Synthesis 1993, 121; Synthesis 1991, 447; Kawaguchi, Synthesis 1985, 701; Micovic et al. Synthesis 1991, 1043).

The acylation of an amino group takes place in the usual way, for example, with an acid halide or acid anhydride optionally in the presence of a base such as dimethylaminopyridine in solvents such as methylene chloride, tetrahydrofuran or pyridine or according to the Scotten Baumann variant in aqueous solution at less alkaline pH.

The introduction of the cyano group can take place with the help of the Sandmeyer reaction; for example, the diazonium salts, intermediately formed from the amino compounds with nitrites, can be reacted with alkali cyanides in the presence of Cu-I-cyanide.

The introduction of the halogens chlorine, bromine or iodine by the amino group can also take place, for example, according to Sandmeyer, by the diazonium salts formed intermediately with nitrites being reacted with Cu(I)chloride or Cu(I)bromide in the presence of the corresponding acid, such as hydrochloric acid or hydrobromic acid, or with potassium iodide.

If an organic nitrous acid ester is used, the halogens can be introduced, e.g., by addition of methylene iodide or tetrabromomethane in a solvent, such as, for example, dimethylformamide.

The introduction of fluorine is possible, for example, by Balz Schiemann reaction of the diazoniumtetrafluoroborate.

The introduction of an $NO_2$ group is possible by a series of known nitration methods. For example, nitration can be performed with nitronium tetrafluoroborate in inert solvents, such as, for example, halogenated hydrocarbons or in sulfolane, glacial acetic acid or acetonitrile. The introduction is also possible, e.g., by nitrating acid in concentrated sulfuric acid as solvent, at temperatures between 0° C. and 30° C.

The introduction of halogen is possible by known halogenation methods, such as, e.g., by electrophilic aromatic substitution.

For example, iodization can be performed according to a process with iodine and iodic acid of Wirth et al. [Liebigs Ann. Chem. 634, 84 (1960)] or with N-iodosuccinimide in solvents such as tetrahydrofuran, dimethylformamide or trifluoromethane sulfonic acid.

The ether cleavage takes place according to usual methods, for example, by reaction with trimethylbromosilane optionally by addition of alkali iodide in an inert solvent such as acetonitrile at a temperature of 0° C. up to the boiling temperature of the solvent.

The introduction of the tetrazole is possible by reaction of the corresponding nitrile with an azide, such as, e.g., trimethylsilylazide, hydrazoic acid or sodium azide, optionally by addition of a proton source such as, e.g., ammonium chloride or triethylammonium chloride in polar solvents such as dimethylformamide, dimethylacetamide or N-methylpyrrolidone at temperatures up to the boiling point of the solvent.

The conversion of the alcohol into the halide is possible with acid halides such as thionyl chloride or phosphorus tribromide with or without solvent. As solvent, halogenated hydrocarbons, e.g., methylene chloride or ether, are possible.

The mixtures of isomers can be separated according to usual methods, such as, for example, crystallization, chromatography or salt formation in the enantiomers or E/Z isomers.

The production of the salts takes place in the usual way, by mixing a solution of the compound of formula I with the equivalent amount or an excess of a base or acid, which optionally is in solution, and the precipitate being separated or the solution being worked up in the usual way.

If the production of the starting compounds is not described, they are known or are analogous to known compounds, for example, according to WO93/08171, or can be produced according to processes described here.

The following examples are to explain the process according to the invention:

PRODUCTION OF STARTING COMPOUNDS

1. A)

2.05 g of mono-tert-butoxycarbonylethylenediamine is heated with 1.25 g (0.86 ml) of 4-fluoro-3-nitro-1- trifluoromethylbenzene for 30 minutes to 50° C. bath temperature. The material is thus solidified. Then, it is chromatographed on silica gel with methylene chloride:ethanol= 10:1. 2.2 g of [1-N-carbo t-butoxy 2 N-(2-nitro-4-trifluoromethylphenyl)]ethylenediamine is obtained.

B)

N-(2-Nitro-4-trifluoromethyl)ethylenediamine, 2.2 g of 1-N-carbo-t-butoxy-2-N-(2-nitro-4-trifluoromethylphenyl) ethylenediamine are heated in 60 ml of ethanol with 60 ml of 1-N-hydrochloric acid for 2 hours to 110° C. After concentration by evaporation, 1.77 g of N-(2-nitro-4-trifluoromethylphenyl)ethylenediamine is obtained as hydrochloride.

C)

[N-1-(Benzoyl)-N-2-(2-nitro-4-trifluoromethylphenyl)] ethylenediamine. 570 mg of N-(2-nitro-4-trifluoromethylphenyl)ethylenediamine hydrochloride is mixed in 15 ml of methylene chloride first with 424 mg of triethylamine and then with 295 mg of benzoyl chloride. After 2 hours of stirring at room temperature, it is extracted twice with water. The organic phase is dried, filtered and concentrated by evaporation. 690 mg of [N-1-(benzoyl)-N-2-(2-nitro-4-trifluoromethylphenyl)]ethylenediamine is obtained.

Produced analogously are:

[N-1-(Methanesulfonyl)-N-2-(2-nitro-4-trifluoromethylphenyl)]ethylenediamine,

N-1-(4-chloro-benzoylamino)-N-2-(2-nitro-4-trifluoromethylphenyl)ethylenediamine, N-1-(nicotinoylamino)-N-2-(2-nitro-4-trifluoromethylphenyl)ethylenediamine, N-1-(phenylsulfonylamino)-N-2-(2-nitro-4-trifluoromethylphenyl)ethylenediamine

2. A)

1-(2-Nitro-4-trifluoromethylphenylamino)-2-methoxyethane 3.75 g of 2-methoxyethylamine and 10.5 g of 4-fluoro-3-nitro-1-trifluoromethylbenzene are heated in 200 ml of water with 10 g of sodium carbonate for 2 hours to 100° C. bath temperature. The product, which can be isolated (9.8 g) by suctioning off, is precipitated during cooling. The aqueous mother liquor is deacidified with 4N hydrochloric acid and extracted three times with 100 ml of ethyl acetate each. The collected organic extracts are dried, filtered and concentrated by evaporation.

Another 2.7 g is obtained. Total yield: 12.5 g of 1-(2-nitro-4-trifluoromethylphenyl)amino-2-methoxyethane.

3. A)

1.1 g of 2,4-difluoronitrobenzene is heated with 2.8 g of aminomethanephosphonic acid diethyl ester for 2 hours to 40° C.

Then, it is chromatographed on silica gel with methylene chloride:ethanol=10:1. 1.6 g of N-(2-nitro-5-fluorophenyl) aminomethanephosphonic acid diethyl ester is obtained.

Produced analogously are:

N-(2-Nitro-4-fluorophenyl)-aminomethanephosphonic acid diethyl ester

1-[N-(2-nitro-4-fluorophenyl)amino]-ethanephosphonic acid diethyl ester

1-[N-(2-nitro-5-fluorophenyl)-amino]-ethanephosphonic acid diethyl ester 1-(2-nitro-4-trifluoromethylphenylamino)-4-methoxypropanephosphonic acid diethyl ester.

B)

331 mg of N-benzophenoniminylmethanephosphonic acid diethyl ester is introduced with 40 mg of aliquat 336 and with 209 mg of 2-methoxy-1-bromoethane and mixed at 0° C. with 280 mg of powdered potassium hydroxide; then, it is stirred at room temperature for 3.5 hours. The batch is mixed with methylene chloride and 180 mg of silica gel, stirred briefly and suctioned off. The filtrate, which is concentrated by evaporation, is chromatographed on silica gel with cyclohexane:ethyl acetate=1:1. 180 mg 2-(N-benzophenoniminyl)- 4-methoxy-propanephosphonic acid diethyl ester is obtained.

C)

2.0 g of 2-(N-benzophenoniminyl)-4-methoxy-propanephosphonic acid diethyl ester is stirred in 30 ml of 1N HCl and 30 ml of diethyl ether for 3 hours at room temperature. The organic phase is separated and the aqueous phase is extracted again with diethyl ether. The organic phase contains benzophenone and is discarded. The aqueous phase is evaporated to dryness, taken up in 15 ml of saturated common salt solution, neutralized with $Na_2CO_3$ and extracted three times with 50 ml of methylene chloride. The organic phase is dried, filtered and concentrated by evaporation, and 800 mg of 2-amino-4-methoxy-propanephosphonic acid diethyl ester is obtained.

4. A)

790 mg of N-(2-nitro-5-fluorophenyl) aminomethanephosphonic acid diethyl ester is mixed in 50 ml of ethanol with 2.5 g of Raney nickel and hydrogenated for 2 hours at room temperature under normal hydrogen pressure. After suctioning-off from the catalyst, it is concentrated by evaporation. 660 mg of N-(2-amino-5-fluorophenyl)aminomethanephosphonic acid diethyl ester is obtained.

Produced analogously are:

N-(2-Amino-4-fluorophenyl)aminomethanephosphonic acid diethyl ester,

1-[(2-amino-4-trifluoromethylphenyl)amino]-4-methoxypropanephosphonic acid diethyl ester 1-[N-(2-amino-4-fluorophenyl)amino]-ethanephosphonic acid diethyl ester 1-[N-(2-amino-5-fluorophenyl)amino]-ethanephosphonic acid diethyl ester 1-(2-amino-4-trifluoromethylphenyl)amino-2-methoxyethane N-1-(methanesulfonyl)-N-2-(2-amino-4-trifluoromethylphenyl)ethylenediamine N-1-(benzoylamino)-N-2-(2-amino-4-trifluoromethylphenyl)ethylenediamine N-1-(4-chloro-benzoylamino)-N-2-(2-amino-4-trifluoromethylphenyl)ethylenediamine N-1-(nicotinoylamino)-N-2-(2-amino-4-trifluoromethylphenyl)ethylenediamine N-1-(phenylsulfonylamino)-N-2-(2-amino-4-trifluoromethylphenyl)ethylenediamine

EXAMPLE 1

(7-Fluoro-1,2,3,4-tetrahydro-2,3-dioxoquinoxalin-1-yl)-methanephosphonic acid diethyl ester 660 mg of N(-2-amino-5-fluorophenyl)-aminomethanephosphonic acid diethyl ester is introduced in 70 ml of absolute tetrahydrofuran with 509 mg of triethylamine. A solution of 685 mg of oxalic acid ethyl ester chloride in 30 ml of tetrahydrofuran is slowly instilled into this solution. The batch is stirred for 4 hours at room temperature. After suctioning-off of the precipitated salts, the filtrate is concentrated by evaporation, boiled in a mixture of 23 ml of ethanol and 23 ml of 1N hydrochloric acid for 2 hours at 110° C. bath temperature. It is evaporated to dryness and the residue is chromatographed on silica gel with methylene chloride:ethanol=10:1. 561 mg of (7-fluoro-1,2,3,4-tetrahydro-2,3-dioxoquinoxalin-1-yl)-methanephosphonic acid diethyl ester is obtained.

Produced analogously are:

(6-Fluoro-1,2,3,4-tetrahydro-2,3-dioxoquinoxalin-1-yl)-methanephosphonic acid diethyl ester 1-[(7-fluoro-1,2,3,4-tetrahydro-2,3-dioxoquinoxalin-1-yl)]ethanephosphonic acid diethyl ester 1-[(6-fluoro-1,2,3,4-tetrahydro-2,3-dioxoquinoxalin-1-yl)]ethanephosphonic acid diethyl ester Produced basically analogously are:

6-Trifluoromethyl-1-(1-methoxyeth-2-yl)-1,2,3,4-tetrahydro-2,3-dioxoquinoxaline 6-trifluoromethyl-1-(1-N-benzoylaminoeth-2-yl)-1,2,3,4-tetrahydro-2,3-dioxoquinoxaline 6-trifluoromethyl-1-(1-N-methanesulfonylaminoeth-2-yl)-1,2,3,4-tetrahydro-2,3-dioxoquinoxaline 1-(6-trifluoromethyl-1,2,3,4-tetrahydro-2,3-dioxoquinoxalin-1-yl)-3-methoxy-propanephosphonic acid diethyl ester 6-trifluoromethyl-1-(1-N-phenylsulfonylaminoeth-2-yl)-1,2,3,4-tetrahydro-2,3-dioxoquinoxaline 6-trifluoromethyl-1-(1-N-nicotinoylamino-2-yl)-1,2,3,4-tetrahydro-2,3-dioxoquinoxaline 6-trifluoromethyl-1-(1-N-4-chloro-benzoylaminoeth-2-yl)-1,2,3,4-tetrahydro-2,3-dioxoquinoxaline

EXAMPLE 2

1 g of 6-trifluoromethyl-1-(1-methoxyeth-2-yl)-1,2,3,4-tetrahydro-2,3-dioxoquinoxaline is mixed in 20 ml of absolute acetonitrile with 3.15 ml of trimethylbromosilane and 1.4 g of sodium iodide and heated for 1 hour to 80° C. bath temperature. After the addition of 25 ml of water, it is extracted with ethyl acetate. The organic phase is separated, concentrated by evaporation and chromatographed on silica gel with toluene:glacial acetic acid:water=10:10:1. After concentration by evaporation of the corresponding fractions and absorptive precipitation with ethanol, 330 mg of 6-trifluoromethyl-1-(1-hydroxyeth-2-yl)-1,2,3,4-tetrahydro-2,3-dioxoquinoxalinedione is obtained.

EXAMPLE 3

615 mg of (7-fluoro-1,2,3,4-tetrahydro-2,3-dioxoquinoxalin-1-yl)methanephosphonic acid diethyl ester is mixed in 60 ml of methylene chloride with 743 mg of nitronium tetrafluoroborate. The batch is stirred for 2 hours at room temperature. It is mixed with 50 ml of water and, after separation of the organic phase, it is extracted three times with methylene chloride. The collected organic phase is dried, filtered and concentrated by evaporation. The residue is chromatographed on silica gel with methylene chloride:ethanol=10:1. 350 mg of (6-nitro-7-fluoro-1,2,3,4-tetrahydro-2,3-dioxoquinoxalin-1-yl)-methanephosphonic acid diethyl ester is obtained.

Produced basically analogously are:

(6-Fluoro-7-nitro-1,2,3,4-tetrahydro-2,3-dioxoquinoxalin-1-yl)methanephosphonic acid diethyl ester 1-[(6-fluoro-7-nitro-1,2,3,4-tetrahydro-2,3-dioxoquinoxalin-1-yl)]ethanephosphonic acid diethyl ester 1-[(7-fluoro-6-nitro-1,2,3,4-tetrahydro-2,3-dioxoquinoxalin-1-yl)]ethanephosphonic acid diethyl ester 1-[(6-trifluoromethyl-7-nitro-1,2,3,4-tetrahydro-2,3-dioxoquinoxalin-1-yl)]ethanephosphonic acid diethyl ester N-[(6-trifluoromethyl-7-nitro-1,2,3,4-tetrahydro-2,3-dioxoquinoxalin-1-yl)]methanephosphonic acid diethyl ester N-[(6-trifluoromethyl-7-nitro-1,2,3,4-tetrahydro-2,3-dioxoquinoxalin-1-yl)]acetonitrile

EXAMPLE 4

140 mg of (6-nitro-7-fluoro-1,2,3,4-tetrahydro-2,3-dioxoquinoxalin-1-yl)methanephosphonic acid diethyl ester is heated with 129 mg of morpholine for 1.5 hours to 120° C. bath temperature. After concentration by evaporation in a vacuum, the residue is chromatographed on silica gel with toluene:glacial acetic acid:water=10:10:1. After concentration by evaporation of the corresponding fractions, 300 mg of (7-morpholino-6-nitro-1,2,3,4-tetrahydro-2,3-dioxoquinoxalin-1-yl)methanephosphonic acid diethyl ester is obtained.

Produced analogously are:

[6-(N-Imidazolyl)-7-nitro-1,2,3,4-tetrahydro-2,3-dioxoquinoxalin-1-yl]methanephosphonic acid diethyl ester 1-[6-(N-imidazolyl)-7-nitro-1,2,3,4-tetrahydro-2,3-dioxoquinoxalin-1-yl]ethanephosphonic acid diethyl ester 1-[7-(N-imidazolyl)-6-nitro-1,2,3,4-tetrahydro-2,3-dioxoquinoxalin-1-yl]ethanephosphonic acid diethyl ester (6-morpholino-7-nitro-1,2,3,4-tetrahydro-2,3-dioxoquinoxalin-1-yl)methanephosphonic acid diethyl ester 1-[(6-morpholino-7-nitro-1,2,3,4-tetrahydro-2,3-dioxoquinoxalin-1-yl)]ethanephosphonic acid diethyl ester 1-[(7-morpholino-6-nitro-1,2,3,4-tetrahydro-2,3-dioxoquinoxalin-1-yl)]ethanephosphonic acid diethyl ester 1-[(7-2-(methoxyethylamino-6-nitro-1,2,3,4-tetrahydro-2,3-dioxoquinoxalin-1-yl)]methanephosphonic acid diethyl ester 1-[(7-N-methylpiperazinyl-6-nitro-1,2,3,4-tetrahydro-2,3-dioxoquinoxalin-1-yl)]methanephosphonic acid diethyl ester 1-[7-(4-methylimidazol-1-yl)-6-nitro-1,2,3,4-tetrahydro-2,3-dioxoquinoxalin-1-yl]methanephosphonic acid diethyl ester 1-[7-(2-methylimidazol-1-yl)-6-nitro-1,2,3,4-tetrahydro-2,3-dioxoquinoxalin-1-yl]methanephosphonic acid diethyl ester 1-[7-(2,4-dimethylimidazol-1-yl)-6-nitro-1,2,3,4-tetrahydro-2,3-dioxoquinoxalin-1-yl]methanephosphonic acid diethyl ester (7-thiomorpholino-6-nitro-1,2,3,4-tetrahydro-2,3-dioxoquinoxalin-1-yl)methanephosphonic acid diethyl ester (7-NN-dipropylamino-6-nitro-1,2,3,4-tetrahydro-2,3-dioxoquinoxalin-1-yl)methanephosphonic acid diethyl ester (7-N,N-dipropylamino-6-nitro-1,2,3,4-tetrahydro-2,3-dioxoquinoxalin-1-yl)ethanephosphonic acid diethyl ester (7-N-methyl-N-propylamino-6-nitro-1,2,3,4-tetrahydro-2,3-dioxoquinoxalin-1-yl)methanephosphonic acid diethyl ester N-[7-(1,2,4-triazol-1-yl)-6-nitro-1,2,3,4-tetrahydro-2,3-quinoxalin-1-yl]methanephosphonic acid diethyl ester

EXAMPLE 5

375 mg of (7-fluoro-6-nitro-1,2,3,4-tetrahydro-2,3-dioxoquinoxalin-1-yl)methanephosphonic acid diethyl ester is added to a solution that was produced from 200 mg of trifluoroethanol, 60 mg of sodium hydride (80%) in 20 ml of absolute tetrahydrofuran. After the addition, it is heated for 4.5 hours to 70° C. bath temperature. It is taken up, concentrated by evaporation, in 50 ml of water, adjusted acidic with 1N hydrochloric acid and extracted three times with ethyl acetate. The organic phase is dried, filtered and concentrated by evaporation. The residue is chromatographed on silica gel with toluene:glacial acetic acid:water=10:10:1. After concentration by evaporation of the corresponding fractions and absorptive precipitation with ethanol, 19 mg of (6-nitro-7-trifluoroethoxy-1,2,3,4-tetrahydro-2,3-dioxoquinoxalin-1-yl)methanephosphonic acid diethyl ester is obtained in the form of the residue.

EXAMPLE 6

259 mg of (6-nitro-7-morpholino-1,2,3,4-tetrahydro-2,3-dioxoquinoxalin-1-yl)methanephosphonic acid diethyl ester is mixed in 10 ml of absolute acetonitrile with 628 mg of trimethylbromosilane and stirred for 1 hour at room temperature. A little water is added, and it is evaporated to dryness. The residue is chromatographed on silanized silica gel with methanol as eluant. 60 mg of (6-nitro-7-morpholino-1,2,3,4-tetrahydro-2,3-dioxoquinoxalin-1-yl) methanephosphonic acid is obtained.

Produced analogously are:

1-(6-Trifluoromethyl-1,2,3,4-tetrahydro-2,3-dioxoquinoxalin-1-yl)-3-methoxypropanephosphonic acid (6-morpholino-7-nitro-1,2,3,4-tetrahydro-2,3-dioxoquinoxalin-1-yl)methanephosphonic acid 1-[(6-morpholino-7-nitro-1,2,3,4-tetrahydro-2,3-dioxoquinoxalin-1-yl)]ethanephosphonic acid 1-[(7-morpholino-6-nitro-1,2,3,4-tetrahydro-2,3-dioxoquinoxalin-1-yl)]ethanephosphonic acid 1-[(7-(2-methoxyethylamino-6-nitro-1,2,3,4-tetrahydro-2,3-dioxoquinoxalin-1-yl)]methanephosphonic acid 1-[(7-N-methylpiperazinyl-6-nitro-1,2,3,4-tetrahydro-2,3-dioxoquinoxalin-1-yl)]methanephosphonic acid (7-thiomorpholino-7-nitro-1,2,3,4-tetrahydro-2,3-dioxoquinoxalin-1-yl)methanephosphonic acid

[(6-trifluoromethyl-7-morpholino-quinoxaline-2,3-dion)-1-yl]-methanephosphonic acid;

Melting point>300° C., $^1$H-NMR in DMSO: 7.9 s, 1H; 7.4 s, 1H; 4.6 d, 11 Hz, 2H; 3.7 t 5 Hz, 2H; 2.9 t, 5 Hz, 2H.

Produced analogously are:

[(6-Trifluoromethyl-7-[piperidin-1-yl]quinoxaline-2,3-dion)-1-yl]-methanephosphonic acid;

Melting point>300° C.;

[(6-trifluoromethyl-7-[2,6-dimethyl-(morpholin-1-yl)] quinoxaline-2,3-dion)-1-yl]-methanephosphonic acid;

[(6-trifluoromethyl-7-(hexahydroazepin-1-yl) quinoxaline-2,3-dion)-1-yl]-methanephosphonic acid;

[(6-trifluoromethyl-7-[(4-phenylpiperazin-1-yl) quinoxaline-2,3-dion)-1-yl]-methanephosphonic acid;

1-[(6-trifluoromethyl-7-[morpholin-1-yl]quinoxaline-2,3-dion)-1-yl]-ethanephosphonic acid;

EXAMPLE 7

250 mg of [(6-(N-imidazolyl)-7-nitro-1,2,3,4-tetrahydro-2,3-dioxoquinoxalin-1-yl)methanephosphonic acid diethyl ester is heated in 3 ml of concentrated hydrochloric acid for 2.5 hours to 110° C. bath temperature. After concentration by evaporation, it is taken up in water, and the precipitated product is suctioned off. 100 mg of [6-(N-imidazolyl)-7-nitro-1,2,3,4-tetrahydro-2,3-dioxoquinoxalin-1-yl] methanephosphonic acid is obtained.

Produced analogously are:

(6-Nitro-7-fluoro-1,2,3,4-tetrahydro-2,3-dioxoquinoxalin-1-yl)methanephosphonic acid (7-nitro-6-fluoro-1,2,3,4-tetrahydro-2,3-dioxoquinoxalin-1-yl)methanephosphonic acid 1-[6-(N-imidazolyl)-7-nitro-1,2,3,4-tetrahydro-2,3-dioxoquinoxalin-1-yl]ethanephosphonic acid 1-[7-(N-imidazolyl)-6-nitro-1,2,3,4-tetrahydro-2,3-dioxoquinoxalin-1-yl]ethanephosphonic acid 1-[(6-fluoro-7-nitro-1,2,3,4-tetrahydro-2,3-dioxoquinoxalin-1-yl)]ethanephosphonic acid 1-[(7-fluoro-6-nitro-1,2,3,4-tetrahydro-2,3-dioxoquinoxalin-1-yl)]ethanephosphonic acid 1-[7-(2-methylimidazol-1-yl)-6-nitro-1,2,3,4-tetrahydro-2,3-dioxoquinoxalin-1-yl]methanephosphonic acid 1-[7-(4-methylimidazol-1-yl)-6-nitro-1,2,3,4-tetrahydro-2,3-dioxoquinoxalin-1-yl]methanephosphonic acid 1-[7-(2,4-dimethylimidazol-1-yl)-6-nitro-1,2,3,4-tetrahydro-2,3-dioxoquinoxalin-1-yl]methanephosphonic acid (7-NN-dipropylamino-6-nitro-1,2,3,4-tetrahydro-2,3-dioxoquinoxalin-1-yl)methanephosphonic acid (7-N,N-dipropylamino-6-nitro-1,2,3,4-tetrahydro-2,3-dioxoquinoxalin-1-yl)methanephosphonic acid (7-N-methyl-N-propylamino-6-nitro-1,2,3,4-tetrahydro-2,3-dioxoquinoxalin-1-yl)methanephosphonic acid 1-[(6-trifluoromethyl-7-imidazolyl-quinoxaline-2,3-dion)-1-yl]ethanphosphonic acid 1-[(6-trifluoromethyl-7-(-4-methylimidazol-1-yl-quinoxaline-2,3-dion)-1-yl]methanephosphonic acid N-[6-trifluoromethyl-7-amino-1,2,3,4-tetrahydro-2,3-dioxoquinoxalin-1-yl]methanephosphonic acid 1-[6-trifluoromethyl-7-amino-1,2,3,4-tetrahydro-2,3-dioxoquinoxalin-1-yl]ethanephosphonic acid 1-[(6-trifluoromethyl-7-[piperidin-1-yl]quinoxaline-2,3-dion)-1yl]-ethanephosphonic acid 1-[(6-trifluoromethyl-7-[piperidin-1-yl]quinoxaline-2,3-dion)-1yl]-acetic acid N-[6-trifluoromethyl-7-amino-1,2,3,4-tetrahydro-2,3-dioxo-quinoxalin-1-yl]-acetic acid 1-[6-trifluoromethyl-7-propylamino-1,2,3,4-tetrahydro-2,3-dioxo-quinoxalin-1-yl]-ethane-1-phosphonic acid 1-[6-trifluoromethyl-7-hexylamino-1,2,3,4-tetrahydro-2,3-dioxo-quinoxalin-1-yl]-ethane-1-phosphonic acid N-[(6-trifluoromethyl-7-[hex-1-ylamino]-quinoxaline-2,3-dion)-1yl]-methanephosphonic acid N-[(6-trifluoromethyl-7-[pent-1-ylamino]-quinoxaline-2,3-dion)-1yl]-methanephosphonic acid N-[(6-trifluoromethyl-7-[hex-2-ylamino]-quinoxaline-2,3-dion)-1yl]-methanephosphonic acid N-[7-(1,2,4-triazol-1-yl)-6-nitro-1,2,3,4-tetrahydro-2,3-quinoxalin-1-yl]methanephosphonic acid

EXAMPLE 8

N-(6 Trifluoromethyl-7-morpholinoquinoxaline-2,3-dion-1-yl)methanephosphonic acid diethyl ester

A 3.3 g (30 mmol) of aminomethanephosphonic acid in 120 ml of water and 120 ml of ethanol are introduced together with 3.37 g (31.8 mmol) of soda and mixed with 7.8 g (97%, 30 mmol) of 3-trifluoromethyl-4,6-dichloronitrobenzene, and it is refluxed for 4 hours at 120° C. bath temperature. After removing the ethanol in a rotary evaporator, it is extracted three times with 100 ml of ethyl acetate. The organic phase is washed with a little water. It contains starting material and is discarded. The collected aqueous phase is adjusted acidic with 4N hydrochloric acid to pH 1 and extracted three times with 100 ml of ethyl acetate each. The organic phase is washed with water, dried, filtered and concentrated by evaporation. 6.85 g (68% of theory) of N-(2-nitro-4-trifluoromethyl-5-chloro-phenyl)-aminomethanephosphonic acid of melting point 207.3° C. is obtained.

Produced analogously is:

1-[(2-Nitro-4-trifluoromethyl-5-chloro-phenyl)-amino] ethanephosphonic acid

B,C 6.85 g (20.5 mmol) of N-(2-nitro-4-trifluoromethyl-5-chloro-phenyl)-aminomethanephosphonic acid is stirred in 20 ml of morpholine for 3.5 hours at 120° C. bath temperature. It is evaporated to dryness in a rotary evaporator, and the residue is heated with 100 ml of orthoformic acid triethyl ester and 779 mg (4.1 mmol) of p-toluenesulfonic acid for 3.8 hours to 150° C. bath temperature. After evaporation to dryness in a rotary evaporator, it is taken up in 100 ml of water, mixed with common salt and extracted three times with 100 ml of ethyl acetate each. The collected ethyl acetate phase is washed with diluted common salt solution, dried, filtered and concentrated by evaporation. Yield of 10.6 g (>100% of theory, also contains morpholine hydrochloride) of N-(2-nitro-4-trifluoromethyl-5-morpholino-phenyl)-aminomethanephosphonic acid diethyl ester.

D 10.6 g (~20 mmol) of N-(2-nitro-4-trifluoromethyl-5-morpholino-phenyl)-aminomethanephosphonic acid diethyl ester is hydrogenated in 250 ml of ethanol for 3.5 hours with 4.5 g of palladium on carbon (10%) with normal hydrogen pressure at room temperature. After suctioning off the catalyst on diatomaceous earth and concentration of the filtrate by evaporation, 9.2 g (>100% of theory, also contains morpholine hydrochloride) of N-(2-amino-4-trifluoromethyl-5-morpholino-phenyl)-aminomethanephosphonic acid diethyl ester is obtained.

Produced analogously via B, C, D are:

N-(2-amino-4-trifluoromethyl-5-piperidino-phenyl)-aminomethanephosphonic acid diethyl ester N-(2-amino-4-trifluoromethyl-5-(2,6-dimethylmorpholino)-phenyl)-aminomethanephosphonic acid diethyl ester N-(2-amino-4-trifluoromethyl-5-hexahydroazepino-phenyl)-aminomethanephosphonic acid diethyl ester N-(2-amino-4-trifluoromethyl-5-phenylpiperazinyl-phenyl)-aminomethanephosphonic acid diethyl ester 1-[(2-amino-4-trifluoromethyl-5-morpholinophenyl)-amino]ethanephosphonic acid diethyl ester N[(2-amino-4-trifluoromethyl-5-hex-1-ylaminophenyl)-amino]methanephosphoric acid diethyl ester N[(2-amino-4-trifluoromethyl-5-pent-1-ylaminophenyl)-amino]methanephosphoric acid diethyl ester N[(2-amino-4-trifluoromethyl-5-hex-2-ylaminophenyl)-amino]methanephosphoric acid diethyl ester

E 1.26 g (2.7 mmmol) of N-(2-amino-4-trifluoromethyl-5-morpholino-phenyl)-aminomethanephosphonic acid diethyl ester is introduced in 60 ml of absolute tetrahydrofuran together with 0.79 ml (5.7 mmol) of triethylamine. The mixture is mixed drop by drop with a solution of 0.63 ml (5.7 mmol) of oxalic acid ethyl ester chloride in 20 ml of tetrahydrofuran. Then, it is stirred for 3 hours at room temperature. The batch is suctioned off and the filtrate concentrated by evaporation. The residue of the filtrate that is concentrated by evaporation is taken up in 20 ml of ethanol and 20 ml of 1N hydrochloric acid and stirred for 2 hours at 110° C. bath temperature. After removal of the ethanol in a vacuum, it is diluted with water to 30 ml and shaken out three times with 30 ml of ethyl acetate each. The collected ethyl acetate phase is washed once with 30 ml of water, dried, filtered and concentrated by evaporation. 1.13 g (89.7% of theory) of [(6-trifluoromethyl-7-morpholinoquinoxaline-2,3-dion)-1-yl]methanephosphonic acid diethyl ester of melting point 192.6° C. is obtained.

Produced analogously are:

[(6-Trifluoromethyl-7-[piperidin-1-yl]quinoxaline-2,3-dion)-1-yl]-methanephosphonic acid diethyl ester;

[(6-trifluoromethyl-7-[2,6-dimethyl-(morpholin-1-yl)] quinoxaline-2,3-dion)-1-yl]-methanephosphonic acid diethyl ester;

[(6-trifluoromethyl-7-(hexahydroazepin-1-yl] quinoxaline-2,3-dion)-1-yl]-methanephosphonic acid diethyl ester;

[(6-trifluoromethyl-7-[(4-phenylpiperazin-1-yl] quinoxaline-2,3-dion)-1-yl]-methanephosphonic acid diethyl ester;

1-[(6-trifluoromethyl-7-[morpholin-1-yl]-quinoxaline-2,3-dion)-1-yl]-ethanephosphonic acid diethyl ester;

N-((6-trifluoromethyl-7-[hex-1-ylamino]-quinoxaline-2,3-dion)-1yl]-methanephosphonic acid diethyl ester N-[(6-trifluoromethyl-7-[pent-1-ylamino]-quinoxaline-2,3-dion)-1yl]-methanephosphonic acid diethyl ester N-[(6-trifluoromethyl-7-[hex-2-ylamino]-quinoxaline-2,3-dion)-1yl]-methanephosphonic acid diethyl ester

EXAMPLE 9

1-(6 Trifluoromethyl-7-imidazolylquinoxaline-2,3-dion-1-yl)-ethanephosphonic acid diethyl ester

A 1.67 g (5 mmol) of 1-[(2-nitro-4-trifluoromethyl-5-chloro-phenyl)amino]ethanephosphonic acid (according to example 8, A) is stirred together with 1.70 g of imidazole for 4 hours at 160° C. bath temperature. It is taken up in 100 ml of water and stirred twice with ion exchanger IR 120 (strong acid form, Amberlite, 20–50 mesh) and suctioned off. Then, it is evaporated to dryness in a rotary evaporator and the residue is heated with 24 ml of orthoformic acid triethyl ester and 156 mg (0.82 mmol) of p-toluene sulfonic acid for 10 hours to 150° C. bath temperature. After evaporation to dryness in a rotary evaporator, it is chromatographed on silica gel with methylene chloride:ethanol=10:1. 222 mg (17% of theory) of 1-[(2-nitro-4-trifluoromethyl-5-imidazolylphenyl)amino]ethanephosphonic acid diethyl ester is obtained.

Produced analogously is:

1-[(2-Nitro-4-trifluoromethyl-5(4-methylimidazol-1-yl)-phenyl)-amino]methanephosphonic acid diethyl ester

B 572 mg (1.4 mmol) of 1-[(2-nitro-4-trifluoromethyl-5-imidazolyl)-phenyl)-amino]ethanephosphonic acid diethyl ester is hydrogenated in 60 ml of ethanol with 300 mg of palladium on carbon (10%) with normal hydrogen pressure at room temperature for 1.5 hours. After suctioning off the catalyst on diatomaceous earth and concentration by evaporation of the filtrate, 531 mg (99.6% of theory) of 1-[(2-amino-4-trifluoromethyl-5-imidazolylphenyl)-amino] ethanephosphonic acid ethyl ester is obtained.

Produced analogously is:

1-[(2-Amino-4-trifluoromethyl-5(4-methylimidazol-1-yl)-phenyl)-amino]methanephosphonic acid diethyl ester

C 531 mg (1.4 mmol) of 1-[(2-amino-4-trifluoromethyl-5-imidazolyl-phenyl)-amino]ethanephosphonic acid diethyl ester in 35 ml of absolute tetrahydrofuran is introduced together with 0.4 ml (2.9 mmol) of triethylamine. The mixture is mixed drop by drop with a solution of 0.32 ml (2.9 mmol) of oxalic acid ethyl ester chloride in 10 ml of tetrahydrofuran. Then, it is stirred for 3 hours at room temperature. The batch is suctioned off and the filtrate concentrated by evaporation. The residue of filtrate, concentrated by evaporation, is taken up in 15 ml of ethanol and 15 ml of 1N hydrochloric acid and stirred for 2 hours at 110° C. bath temperature. It is diluted with water to 30 ml after removal of the ethanol in a vacuum, and it is shaken out three times with 25 ml of ethyl acetate each. The collected ethyl acetate phase is washed once with 30 ml of water, dried, filtered and concentrated by evaporation. 1-[(6-Trifluoromethyl-7-imidazolylquinoxaline-2,3-dion)-1-yl] ethanephosphonic acid diethyl ester is obtained.

Produced analogously is:

1-[(6-Trifluoromethyl-7-(4-methylimidazol-1-yl)quinoxaline-2,3-dion)-1-yl]methanephosphonic acid diethyl ester

EXAMPLE 10

2-[(6 Trifluoromethylquinoxaline-2,3-dion-1-yl) propionitrile]

A 6 g (28.7 mmol) of 4-fluoro-3-nitrobenzotrifluoride is mixed in 120 ml of water with 4.08 g (28.7 mmol) of 3-aminopropionitrile (in the form of fumarate) and 0.36 g (60 mmol) of soda and heated for 3 hours to 110° C. bath temperature. The precipitated solid is suctioned off. 5.1 g (68.5% of theory) of 2-N-[(2-nitro-4-trifluoromethylphenyl) amino]propionitrile is obtained.

B 2 g (7.7 mmol) of 2-N[(2-nitro-4-trifluoromethylphenyl) amino]propionitrile is hydrogenated in 200 ml of ethanol with 500 mg of palladium on activated carbon (10%) for 1.5 hours at room temperature with normal hydrogen pressure. After filtering off of the catalyst and concentration by evaporation of the filtrate, 1.5 g (88.4% of theory) of 2-N[(2-amino-4-trifluoromethylphenyl)amino]propionitrile is obtained.

C 1.5 g (6.5 mmol) of 2-N[(2-amino-4-trifluoromethylphenyl)-amino]propionitrile is introduced with 0.8 ml (7.3 mmol) of triethylamine in 90 ml of tetrahydrofuran and mixed drop by drop at 0° C. with a solution of 0.75 ml (7.3 mmol) of oxalic acid semi-ethyl ester chloride in 20 ml of tetrahydrofuran. After 2 hours of stirring at room temperature, it is suctioned off from the salts and the filtrate is concentrated by evaporation. The residue is refluxed in 100 ml of 1N hydrochloric acid with 100 ml of ethanol for 2 hours. After concentration by evaporation, it is finely divided in ethyl acetate/water, the organic phase is concentrated by evaporation and the residue absorptively precipitated with ethyl acetate. 510 mg (44.8% of theory) of 3-[(6-trifluoromethylquinoxaline-2,3-dion-1-yl) propionitrile is obtained.

Produced analogously are:

2-[(6 Trifluoromethylquinoxaline-2,3-dion-1-yl) acetonitrile

2-[(6 Trifluoromethylquinoxaline-2,3-dion-1-yl)ethyl] sulfonic acid

EXAMPLE 11

2-[(6-Trifluoromethylquinoxaline-2,3-dion-1-yl) ethyl]-tetrazole 345 mg (1.2 mmol) of 3-[(6-trifluoromethylquinoxaline-2,3-dion-1-yl)propionitrile is heated together with 407 mg (6.3 mmol) of sodium azide and 333 mg (6.3 mmol) of ammonium chloride in 13 ml of dimethylformamide for 3 hours to 120° C. bath temperature. After adding once more 203 mg (3.2 mmol) of sodium azide and 160 mg (3.1 mmol) of ammonium chloride, it is heated for 5 hours more to 120° C. bath temperature. After dilution with water and adjusting the pH to 2, it is extracted with ethyl acetate. During the shaking out with saturated common salt solution, the desired compound is precipitated from the organic phase. By concentration by evaporation of the organic phase and absorptive precipitation in ethyl acetate, another fraction is obtained. Altogether, 150 mg (37.8% of theory) of 2-[(6 trifluoromethylquinoxaline-2,3-dion-1-yl)ethyl]-tetrazole of melting point 279.8° C. is obtained.

Produced analogously is:

[(6-Trifluoromethylquinoxaline-2,3-dion-1-yl)methyl]-tetrazole

EXAMPLE 12

2-[(6-Trifluoromethylquinoxaline-2,3-dion-1-yl) ethyl chloride 1.3 g (4.7 mmol) of 2-[(6 trifluoromethylquinoxaline-2,3-dion-1-yl)ethyl alcohol is stirred in 20 ml of thionyl chloride for 4 hours at room temperature. After concentration by evaporation and subsequent distillation with toluene, 1.34 g (97% of theory) of 2-[(6 trifluoromethylquinoxaline-2,3-dion-1-yl)ethyl chloride is obtained.

EXAMPLE 13

N-[(6-Trifluoromethylquinoxaline-2,3-dion-1-yl) ethylimidazole 392 mg (1 mmol) of 2-[(6 trifluoromethylquinoxaline-2,3-dion-1-yl)ethyl chloride is heated with 150 mg (2.2 mmol) of imidazole for 3 hours to 150° C. bath temperature. The organic phase is concentrated by evaporation with dispersion in 10 ml of ethyl acetate and 10 ml of water, and the residue is chromatographed on silica gel with methanol:butanol:water:ammonia=75:25:17:3 as eluant. 54 mg (17% of theory) of 2-((6 trifluoromethylquinoxaline-2, 3-dion-1-yl)ethylimidazole of melting point>250° C. is obtained.

Produced analogously is:

2-[(6 Trifluoromethylquinoxaline-2,3-dion-1-yl) ethylmorpholine (as resin).

EXAMPLE 14

6-Trifluoromethyl-7-nitro-1-(1-methoxyeth-2-yl)-1, 2,3,4-tetrahydro-2,3-dioxoquinoxaline 100 mg of 6-trifluoromethyl-1-(1-methoxyeth-2-yl)-1,2, 3,4-tetrahydro-2,3-dioxoquinoxaline is suspended in 1 ml of concentrated sulfuric acid, mixed at 4° C. with 0.1 ml of a mixture of concentrated sulfuric acid:concentrated nitric acid 1:1 and stirred for 1 hour at 4° C. Then, everything is dissolved. Then, it is poured on ice and the settled precipitate is suctioned off. 59 mg (50% of theory) of 6-trifluoromethyl-7-nitro-1-(1-methoxyeth-2-yl)-1,2,3,4-tetrahydro-2,3-dioxoquinoxaline is obtained.

EXAMPLE 15

6-Trifluoromethyl-7-iodo-1-(1-methoxyeth-2-yl)-1, 2,3,4-tetrahydro-2,3-dioxoquinoxaline 288 mg of 6-trifluoromethyl-1-(1-methoxyeth-2-yl)-1,2, 3,4-tetrahydro-2,3-dioxoquinoxaline is mixed in 5 ml of glacial acetic acid with 0.05 ml of water, 0.012 ml of concentrated sulfuric acid, 34.4 mg of iodic acid and 88.4 mg of iodine and heated for 4 hours to 80° C. After concentration by evaporation, it is taken up in water, adjusted alkaline and extracted with methylene chloride. The organic phase is dried, filtered and concentrated by evaporation and the residue is chromatographed on silica gel with toluene:glacial acetic acid:water=10:10:1 as eluant. 40 mg of 6-trifluoromethyl-7-iodo-1-(1-methoxyeth-2-yl)-1,2, 3,4-tetrahydro-2,3-dioxoquinoxaline is obtained. The residue is starting material, which can be used again in the reaction.

EXAMPLE 16

N-[(6 Cyanoquinoxaline-2,3-dion)-1-yl] ethanephosphonic acid diethyl ester

A 2.77 g (15.24 mmol) of 4-chloro-3-nitrobenzonitrile is stirred with 10.5 g (38 mmol) of 1-aminoethanephosphonic acid diethyl ester for 16 hours at 30° C. The reaction mixture is then chromatographed on silica gel with methylene chloride:ethanol=95:5 as eluant. 3.86 g (80% of theory) of 1-[N-(2-nitro-4-cyanophenyl)amino]ethanephosphonic acid diethyl ester is obtained.

B 3.1 g of N-(2-nitro-4-cyanophenyl) aminoethanephosphonic acid diethyl ester is dissolved in 55 ml of tetrahydrofuran with 3 ml of triethylamine and mixed drop by drop at 0° C. with a solution of 2.35 ml of oxalic acid semi-ethyl ester chloride in 16 ml of tetrahydrofuran. After three days of stirring at room temperature, it is diluted with 300 ml of ethyl acetate and washed in succession with water and concentrated common salt solution. The organic phase is dried, filtered and concentrated by evaporation. 5.43 g of crude N-(diethylphosphonyleth-1-yl)-N-(2-nitro-4-cyanophenyl)oxalic acid semi-ethyl-ester amide, which is reacted again without further purification, is obtained.

C 1.25 g of N-(diethylphosphonyleth-1-yl)-N-(2-nitro-4-cyanophenyl)oxalic acid semi-ethyl ester amide is mixed in 60 ml of glacial acetic acid with 12.9 g (230 mmol) of iron powder and heated for 60 minutes to 90° C. After decanting of the unreacted iron and filtration on diatomaceous earth, the filtrate is concentrated by evaporation, taken up in ethyl acetate and washed several times with water. The organic phase is dried, filtered, and concentrated by evaporation. The residue is chromatographed on silica gel with toluene:ethanol=8:2 as eluant. 1.43 g (32.9% of theory) of N-[(6 cyanoquinoxaline-2,3-dion)-1-yl]ethanephosphonic acid diethyl ester is obtained.

EXAMPLE 17

N-[(6 Cyanoquinoxaline-2,3-dion)-1-yl] ethanephosphonic acid 600 mg of N-[(6 cyanoquinoxaline-2,3-dion)-1-yl] ethanephosphonic acid diethyl ester is dissolved in 20 ml of methylene chloride and slowly mixed drop by drop with 2 ml (13.4 mmol) of trimethylsilyliodide. After 4 hours of stirring at room temperature, a brown solution is produced. It is shaken out with water and the precipitation resulting here is suctioned off. The combined crystallizates are recrystallized from ethanol/water. 300 mg (83% of theory) of N-[(6-cyanoquinoxaline-2,3-dion)-1-yl]ethanephosphonic acid of melting point 280° C. is obtained.

EXAMPLE 18

N-[6-Trifluoromethyl-7-amino-1,2,3,4-tetrahydro-2, 3-dioxoquinoxalin-1-yl]-methanephosphonic acid diethyl ester 600 mg of N-[6-trifluoromethyl-7-nitro-1,2,3,4-tetrahydro-2,3-dioxoquinoxalin-1-yl]-methanephosphonic acid ester is dissolved in 30 ml of ethanol and together with 100 mg of Pd/C (10%) is hydrogenated for 1 hour at normal hydrogen pressure and room temperature. After suctioning off from the catalyst, the catalyst is boiled out again with ethanol, the collected filtrate is concentrated by evaporation, and 590 mg of N-[6-trifluoromethyl-7-amino-1,2,3,4-tetrahydro-2,3-dioxoquinoxalin-1-yl]-ethanephosphonic acid diethyl ester is obtained.

Produced analogously are:

N-[6-Trifluoromethyl-7-amino-1,2,3,4-tetrahydro-2,3-dioxoquinoxalin-1-yl]-methanephosphonic acid diethyl ester N-[6-trifluoromethyl-7-amino-1,2,3,4-tetrahydro-2,3-dioxoquinoxalin-1-yl]-acetic acid ethyl ester 6-trifluoromethyl-7-amino-1-(1-methoxyeth-2-yl)-1,2,3, 4-tetrahydro-2,3-dioxoquinoxaline

EXAMPLE 19

N-[6-Trifluoromethyl-7-nitro-1,2,3,4-tetrahydro-2,3-dioxoquinoxalin-1-yl]-acetic acid ethyl ester

A.)

(1.1 mmol) of 2-[(6 trifluoromethylquinoxaline-2,3-dion-1-yl)acetonitrile is refluxed in 10 ml of concentrated hydrochloric acid for 4 hours. The precipitated product is suctioned off. 188 mg of 2-[(6 trifluoromethylquinoxaline-2,3-dion-1-yl]-acetic acid is obtained.

B.)

150 mg (0.52 mmol) of 2-[(6 trifluoromethylquinoxaline-2,3-dion-1-yl]acetic acid is refluxed in 7 ml of ethanolic hydrochloric acid for 2 hours. Then, it is concentrated by evaporation, the residue is dissolved in 4 ml of methylene chloride and 1 ml of acetonitrile, mixed with 120 mg of nitronium tetrafluoroborate and stirred for two hours at room temperature. Then, it is shaken out with water, dried, filtered and concentrated by evaporation. N-[6-Trifluoromethyl-7-nitro-1,2,3,4-tetrahydro-2,3-dioxoquinoxalin-1-yl]-acetic acid ethyl ester is obtained.

EXAMPLE 20

6-Trifluoromethyl-7-iodo-1-(1-methoxyeth-2-yl-1,2,3,4-tetrahydro-2,3-dioxo-quinoxaline.

90 mg of 6-trifluoromethyl-7-amino-1-(1-methoxyeth-2-yl-1,2,3,4-tetrahydro-2,3-dioxoquinoxaline is taken up in 8 ml of ethanolic hydrochloric acid and concentrated by evaporation, and the hydrochloride is taken up in 6 ml of dimethylformamide and 3 ml of methylene iodide and mixed at 80° C. bath temperature with 0.08 ml of i-amylnitrite. After 3 hours of stirring at this temperature, the batch is concentrated by evaporation in a vacuum. 105 mg of 6-trifluoromethyl-7-iodo-1-(1-methoxyeth-2-yl-1,2,3,4-tetrahydro-2,3-dioxo-quinoxaline is obtained.

Produced analogously are:

N-[6-Trifluoromethyl-7-iodo-1,2,3,4-tetrahydro-2,3-dioxo-quinoxalin-1-yl]-methanephosphonic acid diethyl ester N-[6-trifluoromethyl-7-iodo-1,2,3,4-tetrahydro-2,3-dioxo-quinoxalin-1-yl]-acetic acid ethyl ester

EXAMPLE 21

1-[(6-Trifluoromethyl-7-[piperidin-1-yl]quinoxaline-2,3-dion)-1yl]-ethanephosphonic acid diethyl ester;

At 0° C., a solution of 0.15 ml of a 25% aqueous solution of glutaric dialdehyde and 0.45 ml of 3M sulfuric acid in 3 ml of tetrahydrofuran:methanol=2:3 is instilled in a suspension of 100 mg of [(6-trifluoromethyl-7-amino-1-yl]quinoxaline-2,3-dion)-1yl]-methanephosphonic acid diethyl ester and 30 mg of sodium borohydride tablets in 3 ml of tetrahydrofuran. After the reaction dies down, 30 mg of sodium borohydride tablets are thrown in again and then stirred for 1 hour at room temperature. Then, it is set neutral with sodium hydroxide solution and shaken out with ethyl acetate. The ethyl acetate phase is dried, filtered and concentrated by evaporation. After chromatography on silica gel with toluene:glacial acetic acid:water=10:10:1, 60 mg of 1-[(6-trifluoromethyl-7-[piperidin-1-yl]quinoxaline-2,3-dion)-1yl]-ethanephosphonic acid diethyl ester is obtained.

Produced analogously is:

1-[(6-Trifluoromethyl-7-[piperidin-1-yl]quinoxaline-2,3-dion)-1yl]-acetic acid ethyl ester;

EXAMPLE 22

1-[(6-Trifluoromethyl-7-propylamino-]quinoxaline-2,3-dion)-1yl]ethanephosphonic acid diethyl ester;

At 4° C., a solution of 0.02 ml of distilled propanal and 0.2 ml of 3M sulfuric acid in 2 ml of tetrahydrofuran is instilled in a suspension of 80 mg of [(6-trifluoromethyl-7-amino-1-yl]quinoxaline-2,3-dion)-1yl-methanephosphonic acid diethyl ester in 3 ml of tetrahydrofuran. 20 mg of sodium borohydride tablets are added to this stirred mixture. After the reaction dies down, 10 mg of sodium borohydride tablets are thrown in again and then stirred for 1 hour at room temperature. Then, it, is set neutral with sodium hydroxide solution and shaken out with ethyl acetate. The ethyl acetate phase is dried, filtered and concentrated by evaporation. After chromatography on silica gel with toluene: glacial acetic acid:water=10:10:1, 40 mg of 1-[(6-trifluoromethyl-7-propylamino-quinoxaline-2,3-dion)-1yl]-ethanephosphonic acid diethyl ester is obtained.

EXAMPLE 23

1-[(6-Trifluoromethyl-7-acetylamino-]quinoxaline-2,3-dion)-1yl]-ethanephosphonic acid diethyl ester 80 mg of 1-[(6-trifluoromethyl-7-amino-]quinoxaline-2,3-dion)-1yl]-ethanephosphonic acid diethyl ester is dissolved in 8 ml of acetic acid and mixed with 150 mg of acetic anhydride and stirred for 3 hours at room temperature. After concentration by evaporation, 50 mg of 1-[(6-trifluoromethyl-7-acetylamino-]quinoxaline-2,3-dion)-1yl]-ethanephosphonic acid diethyl ester is obtained.

We claim:

1. A compound of formula I

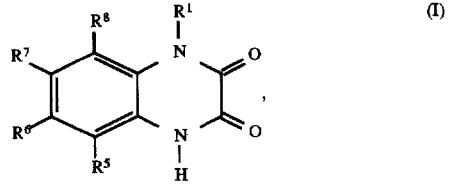

in which $R^1$ means —$(CH_2)_n$—$CR^2H$—$(CH_2)_m$—Z, $R^5$, $R^6$, $R^7$ and $R^8$ are the same or different and mean hydrogen, $C_{1-6}$ alkyl, $CF_3$, nitro, halogen, $NR^9R^{10}$, cyano, $SO_pR^{11}$, $SO_2NR^{12}R^{13}$, $SO_3H$, $SO_3C_{1-6}$ alkyl or $OR^{14}$, $R^2$ means hydrogen or —$(CH_2)_q$—$R^3$, $R^3$ means hydrogen, hydroxy, $C_{1-6}$ alkoxy or $NR^{15}R^{16}$, n, m and q each mean 0, 1, 2 or 3, Z means POXY, OPOXY, NH—$COR^{20}$, NH—$SO_2R^{21}$ or $SO_2R^{22}$, $R^{11}$ means H, $C_{1-6}$ alkyl or phenyl, p means 0, 1 or 2, $R^{12}$ and $R^{13}$ mean hydrogen or $C_{1-4}$ alkyl, $R^{14}$ means H or $C_{1-6}$ alkyl optionally substituted one to three times with halogen, $R^{20}$ and $R^{21}$ mean $C_{1-6}$ alkyl, phenyl or a six-membered ring heteroaromatic group optionally substituted with halogen, $R^{22}$ means hydroxy, $C_{1-6}$ alkoxy or $NR^{24}R^{25}$, X and Y are the same or different and mean hydroxy, $C_{1-6}$ alkoxy, $C_{1-4}$ alkyl or $NR^{18}R^{19}$, $R^9$ and $R^{10}$ are the same or different and mean hydrogen, CO—$C_{1-6}$ alkyl, phenyl or $C_{1-6}$ alkyl that can optionally be substituted with $C_{1-4}$ alkoxy or an amino group optionally mono- or disubstituted with $C_{1-4}$ alkyl, or together with the nitrogen atom forms a 5- to 7-membered saturated heterocycle, optionally having another N, S or O ring atom and optionally substituted one to three times by $C_{1-4}$-alkyl or phenyl, or forms an unsaturated 5-membered heterocycle containing 1–3 ring N atoms and optionally substituted once or twice by cyano, $C_{1-4}$ alkyl, phenyl or —$CO_2C_{1-6}$ alkyl, $R^{15}$ and $R^{16}$, $R^{18}$ and $R^{19}$ are the same or different and mean hydrogen, $C_{1-4}$ alkyl, phenyl or together with the nitrogen atom forms a 5- to 7-membered saturated heterocycle, optionally having another oxygen, sulfur or nitrogen ring atom and optionally substituted one to three times by $C_{1-4}$ alkyl or phenyl, or forms an unsaturated 5-membered heterocycle containing 1–3 N ring atoms and optionally substituted once or twice by cyano, $C_{1-4}$ alkyl, phenyl or —$CO_2C_{1-6}$ alkyl, $R^{24}$ and $R^{25}$ are the same or different and mean hydrogen, $C_{1-4}$ alkyl or together with the nitrogen atom forms a saturated 5- to 7-membered heterocycle optionally having another oxygen, sulfur or nitrogen ring atom and optionally substituted one to three times by $C_{1-4}$ alkyl or phenyl, as well as their isomers or salts, provided that:

if $R^2$ is hydrogen and Z is POXY, $R^5$–$R^8$ do not mean hydrogen;

if $R^2$ means hydrogen, Z means POXY, and $R^5$, $R^6$, $R^7$ or $R^8$ mean only $CF_3$, $NO_2$, halogen, $NH_2$ or methyl, at least two of $R^5$–$R^8$ are not hydrogen;

if $R^1$ is methanephosphonic acid, is $R^6$ cyano or substituted imidazole, $R^5$, $R^7$ and $R^8$ cannot be hydrogen at the same time; and if $R^1$ is methanephosphonic acid, $R^6$ is $CF_3$ or $NO_2$ and $R^7$ is imidazole, $R^5$ and $R^8$ cannot be hydrogen at the same time.

2. A compound of claim 1, which is:

(6-Nitro-7-trifluoroethoxy-1,2,3,4-tetrahydro-2,3-dioxo-quinoxalin-1-yl)-methanephosphonic acid diethyl ester, (6-nitro-7-morpholino-1,2,3,4-tetrahydro-2,3-dioxo-quinoxalin-1-yl)methanephosphonic acid, 1-[7-morpholino-6-nitro-1,2,3,4-tetrahydro-2,3-dioxoquinoxalin-1-yl]ethanephosphonic acid, 1-[(7-(2-methoxyethylamino)-6-nitro-1,2,3,4-tetrahydro-2,3-dioxoquinoxalin-1-yl)]-methanephosphonic acid,

[(6-trifluoromethyl-7-morpholinoquinoxaline-2,3-dion)-1-yl]methanephosphonic acid,

[(6-trifluoromethyl-7-[piperidin-1-yl]quinoxaline-2,3-dion)-1-yl]-methanephosphonic acid,

[(6-trifluoromethyl-7-[2,6-dimethyl-(morpholin-1-yl)]quinoxaline-2,3-dion)-1-yl]methanephosphonic acid,

[(6-trifluoromethyl-7-[azepin-1-yl]quinoxaline-2,3-dion)-1-yl]methanephosphonic acid,

[(6-trifluoromethyl-7-[4-phenylpiperazin-1-yl]quinoxaline-2,3-dion)-1-yl]-methanephosphonic acid, 1-[(6-trifluoromethyl-7-[morpholin-1-yl]-quinoxalin-2,3-dion)-1-yl]-ethanephosphonic acid, 1-[(6-trifluoromethyl-7-imidazolylquinoxaline-2,3-dion)-1-yl]ethanephosphonic acid 1-[(6-trifluoromethyl-7-(4-methylimidazol-1-yl) quinoxaline-2,3-dion)-1-yl]methanephosphonic acid, N-[6-trifluoromethyl-7-amino-1,2,3,4-tetrahydro-2,3-dioxo-quinoxalin-1-yl]methanephosphonic acid, 1-[7-(2-methylimidazol-1-yl)-6-nitro-1,2,3,4-tetrahydro-2,3-dioxoquinoxalin-1-yl]methanephosphonic acid, 1-[7-(4-methylimidazol-1-yl)-6-nitro-1,2,3,4-tetrahydro-2,3-dioxoquinoxalin-1-yl]methanephosphonic acid, or 1-[7-(2,4-dimethylimidazol-1-yl)-6-nitro-1,2,3,4-tetrahydro-2,3-dioxoquinoxalin-1-yl]methanephosphonic acid.

3. A pharmaceutical composition comprising a compound of formula I according to claim 1 and a suitable pharmaceutical vehicle.

4. A process for the production of a compound of formula I of claim 1, which comprises a) cyclizing a compound of formula II

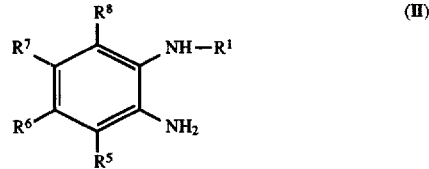

in which $R^1$–$R^3$ and $R^5$–$R^8$ have the meaning given in claim 1, with oxalic acid or reactive oxalic acid derivatives or b) nucleophilically substituting a compound of formula III

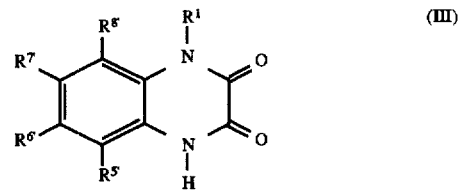

in which $R^1$ has the meaning given in claim 1 and one of substituents $R^{5'}$, $R^{6'}$, $R^{7'}$ or $R^{8'}$ represents a leaving group selected from a halogen, o-mesylate, o-tosylate, o-triflate and o-nonaflate, and then optionally saponifying the ester group, esterifying or amidating the acid group, reducing the nitro group to the amino group, alkylating or acylating the amino group, exchanging the amino group for halogen or cyano, introducing a nitro group, introducing halogen, performing an ether cleavage, converting the alcohol into a halide, nucleophically substituting this halogen, converting a nitrile into the tetrazole, separating the isomers and/or forming the salts.

5. A compound of claim 1, wherein at least two of $R^5$–$R^8$ are other than hydrogen.

6. A compound of claim 1, wherein $R^6$ and/or $R^7$ are other than hydrogen.

7. A compound of claim 1, wherein at least one of $R^5$–$R^8$ is $NR^9R^{10}$ or $CF_3$.

8. A method of treating a disease caused by hyperactivity of an excitatory amino acid which comprises administering an effective amount of a compound of claim 1.

9. The method of claim 8, wherein the disease is a neurological or psychiatric disorder triggered by overstimulation of the AMPA receptor.

10. A compound of formula I

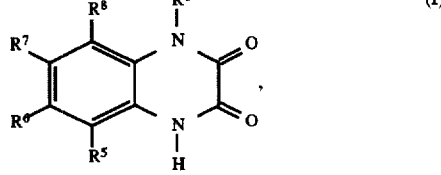

in which $R^1$ means —$(CH_2)_n$—$CR^2H$—$(CH_2)_m$—Z, $R^5$, $R^6$, $R^7$ and $R^8$ are the same or different and mean hydrogen, $C_{1-6}$ alkyl, $CF_3$, nitro, halogen, $NR^9R^{10}$, cyano, $SO_pR^{11}$, $SO_2NR^{12}R^{13}$, $SO_3H$, $SO_3C_{1-6}$ alkyl or $OR^{14}$, provided that at least one of $R^5$–$R^8$ is $NR^9R^{10}$ where $R^9R^{10}$ form a heterocycle with the N atom, $R^2$ means hydrogen or —$(CH_2)_q$—$R^3$, $R^3$ means hydrogen, hydroxy, $C_{1-6}$ alkoxy or $NR^{15}R^{16}$, n, m and q each mean 0, 1, 2 or 3, Z means POXY, $R^{11}$ means H, $C_{1-6}$ alkyl or phenyl, p means 0, 1 or 2, $R^{12}$ and $R^{13}$ mean hydrogen or $C_{1-4}$ alkyl, $R^{14}$ means H or $C_{1-6}$ alkyl optionally substituted one to three times with halogen, X and Y are the same or different and mean hydroxy, $C_{1-6}$ alkoxy, $C_{1-4}$ alkyl or $NR^{18}R^{19}$, $R^9$ and $R^{10}$ are the same or different and mean hydrogen, CO—$C_{1-6}$ alkyl, phenyl or $C_{1-6}$ alkyl that can optionally be substituted with $C_{1-4}$ alkoxy or an amino group optionally mono- or disubstituted with $C_{14}$ alkyl, or together with the nitrogen atom forms a 5- to 7-membered saturated heterocycle, optionally having another N, S or O ring atom and optionally substituted one to three times by $C_{1-4}$-alkyl or phenyl, or forms an unsaturated 5-membered heterocycle containing 1–3 ring N atoms and optionally substituted once or twice by cyano, $C_{1-4}$ alkyl, phenyl or —$CO_2C_{1-6}$ alkyl $R^{15}$, $R^{16}$, $R^{18}$ and $R^{19}$ are the same or different and mean hydrogen, $C_{1-4}$ alkyl, phenyl or together with the nitrogen atom forms a 5- to 7-membered saturated heterocycle, optionally having another oxygen, sulfur or nitrogen ring atom and optionally substituted one to three times by $C_{1-4}$ alkyl or phenyl, or forms an unsaturated 5-membered heterocycle containing 1–3 N ring atoms and optionally substituted once or twice by cyano, $C_{1-4}$ alkyl, phenyl or —$CO_2C_{1-6}$ alkyl, provided that:

if $R^1$ is methanephosphonic acid and $R^6$ is cyano or substituted imidazole, $R^5$, $R^7$ and $R^8$ cannot be hydrogen at the same time; and if $R^1$ is methanephosphonic acid, $R^6$ is $CF_3$ or $NO_2$ and $R^7$ is imidazole, $R^5$ and $R^8$ cannot be hydrogen at the same time.

11. A compound of claim 10, which is:

(6-nitro-7-morpholino-1,2,3,4-tetrahydro-2,3-dioxoquinoxalin-1-yl)methanephosphonic acid, 1-[7-morpholino-6-nitro-1,2,3,4-tetrahydro-2,3-dioxoquinoxalin-1-yl]ethanephosphonic acid,

[(6-trifluoromethyl-7-morpholinoquinoxaline-2,3-dion)-1-yl]methanephosphonic acid,

[(6-trifluoromethyl-7-[piperidin-1-yl]quinoxaline-2,3-dion)-1-yl]-methanephosphonic acid,

[(6-trifluoromethyl-7-[2,6-dimethyl-(morpholin-1-yl)]quinoxaline-2,3-dion)-1-yl]methanephosphonic acid,

[(6-trifluoromethyl-7-[azepin-1-yl]quinoxaline-2,3-dion)-1-yl]methanephosphonic acid,

[(6-trifluoromethyl-7-[4-phenylpiperazin-1-yl]quinoxaline-2,3-dion)-1-yl]methanephosphonic acid, 1-[(6-trifluoromethyl-7-[morpholin-1-yl]-quinoxalin-2,3-dion)-1-yl]ethanephosphonic acid, 1-[(6-trifluoromethyl-7-imidazolylquinoxaline-2,3-dion)-1-yl]ethanephosphonic acid 1-[(6-trifluoromethyl-7-(4-methylimidazol-1-yl)quinoxaline-2,3-dion)-1-yl]methanephosphonic acid, 1-[7-(2-methylimidazol-1-yl)-6-nitro-1,2,3,4-tetrahydro-2,3-dioxoquinoxalin-1-yl]methanephosphonic acid, 1-[7-(4-methylimidazol-1-yl)-6-nitro-1,2,3,4-tetrahydro-2,3-dioxoquinoxalin-1-yl]methanephosphonic acid, or 1-[7-(2,4-dimethylimidazol-1-yl)-6-nitro-1,2,3,4-tetrahydro-2,3-dioxoquinoxalin-1-yl]methanephosphonic acid.

12. A pharmaceutical composition comprising a compound of formula I according to claim 10, and a suitable pharmaceutical vehicle.

13. A process for the production of a compound of formula I of claim 10, which comprises a) cyclizing a compound of formula II

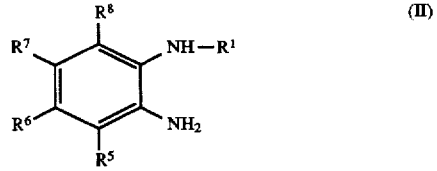

in which $R^1$–$R^3$ and $R^5$–$R^8$ have the meaning given in claim 10, with oxalic acid or reactive oxalic acid derivatives or b) nucleophilically substituting a compound of formula III

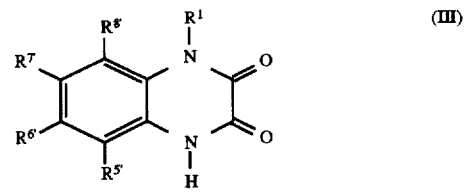

in which $R^1$ has the meaning given in claim 10 and one of substituents $R^5$, $R^6$, $R^7$ or $R^8$ represents a leaving group selected from a halogen, o-mesylate, o-tosylate, o-triflate or o-nonaflate, and then optionally saponifying the ester group, esterifying or amidating the acid group, reducing the nitro group to the amino group, alkylating or acylating the amino group, exchanging the amino group for halogen or cyano, introducing a nitro group, introducing halogen, performing an ether cleavage, converting the alcohol into a halide, nucleophically substituting this halogen, converting a nitrile into the tetrazole, separating the isomers and/or forming the salts.

14. A compound of claim 10, wherein at least two of $R^5$–$R^8$ are other than hydrogen.

15. A compound of claim 10, wherein $R^6$ and/or $R^7$ are other than hydrogen.

16. A method of treating a disease caused by hyperactivity of an excitatory amino acid which comprises administering an effective amount of a compound of claim 10.

17. The method of claim 16, wherein the disease is a neurological or psychiatric disorder triggered by overstimulation of the AMPA receptor.

18. A compound of formula I

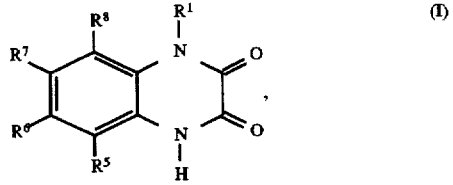

in which $R^1$ means —$(CH_2)_n$—$CR^2H$—$(CH_2)_m$—Z, $R^5$, $R^6$, $R^7$ and $R^8$ are the same or different and mean hydrogen, $C_{1-6}$ alkyl, $CF_3$, nitro, halogen, $NR^9R^{10}$, cyano, $SO_pR^{11}$, $SO_2NR^{12}R^{13}$, $SO_3H$, $SO_3C_{1-6}$ alkyl or $OR^{14}$, $R^2$ means hydrogen or —$(CH_2)_q$—$R^3$, $R^3$ means hydrogen, hydroxy, $C_{1-6}$ alkoxy or $NR^{15}R^{16}$, n, m and q each mean 0, 1, 2 or 3, Z means $OR^{17}$, $NR^{18}R^{19}$, tetrazole, halogen or cyano, $R^{11}$ means H, $C_{1-6}$ alkyl or phenyl, p means 0, 1 or 2, $R^{12}$, $R^{13}$ and $R^{17}$ mean hydrogen or $C_{1-4}$ alkyl, $R^{14}$ means H or $C_{1-6}$ alkyl optionally substituted one to three times with halogen, $R^9$ and $R^{10}$ are the same or different and mean hydrogen, CO—$C_{1-6}$ alkyl, phenyl or $C_{1-6}$ alkyl that can optionally be substituted with $C_{1-4}$ alkoxy or an amino group optionally mono- or disubstituted with $C_{1-4}$ alkyl, or together with the nitrogen atom forms a 5- to 7-membered saturated heterocycle, optionally having another N, S or O ring atom and optionally substituted one to three times by $C_{1-4}$-alkyl or phenyl, or forms an unsaturated 5-membered heterocycle containing 1–3 ring N atoms and optionally substituted once or twice by cyano, $C_{1-4}$ alkyl, phenyl or —$CO_2C_{1-6}$ alkyl, $R^{15}$ and $R^{16}$ are the same or different and mean hydrogen, $C_{1-4}$ alkyl, phenyl or together with the nitrogen atom form a 5- to 7-membered saturated heterocycle, optionally having another oxygen, sulfur or nitrogen ring atom and optionally substituted one to three times by $C_{1-4}$ alkyl or phenyl, or forms an unsaturated 5-membered heterocycle containing 1–3 N ring atoms and optionally substituted once or twice by cyano, $C_{1-4}$ alkyl, phenyl or —$CO_2C_{1-6}$ alkyl, provided that:

$R^5$–$R^8$ are not simultaneously hydrogen; and if $R^5$, $R^6$, $R^7$ or $R^8$ is $CF_3$, halogen, cyano, $OR^{14}$, $NO_2$ or $CH_3$, then at least one of the other $R^5$–$R^8$ is $NR^9R^{10}$, $SO_pR^{11}$, $SO_2NR^{12}R^{13}$, $SO_3H$, or $SO_3C_{1-6}$ allyl, but $NR^9R^{10}$ is not pyrrole, imidazole or triazole.

19. A pharmaceutical composition comprising a compound of formula I according to claim 18, and a suitable pharmaceutical vehicle.

20. A process for the production of a compound of formula I of claim 18, which comprises a) cyclizing a compound of formula II

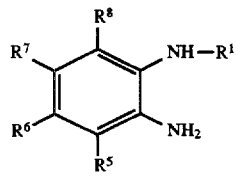

(II)

in which $R^1$–$R^3$ and $R^5$–$R^8$ have the meaning given in claim 18, with oxalic acid or reactive oxalic acid derivatives or b) pucleophilically substituting a compound of formula III

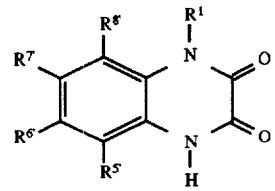

(III)

in which $R^1$ has the meaning given in claim 18 and one of substituents $R^{5'}$, $R^{6'}$, $R^{7'}$ or $R^{8'}$ represents a leaving group selected from a halogen, o-mesylate, o-tosylate, o-triflate or o-nonaflate, and then optionally saponifying the ester group, esterifying or amidating the acid group, reducing the nitro group to the amino group, alkylating or acylating the amino group, exchanging the amino group for halogen or cyano, introducing a nitro group, introducing halogen, performing an ether cleavage, converting the alcohol into a halide, nucleophically substituting this halogen, converting a nitrile into the tetrazole, separating the isomers and/or forming the salts.

21. A compound of claim 18, wherein at least two of $R^5$–$R^8$ are other than hydrogen.

22. A compound of claim 18, wherein $R^6$ and/or $R^7$ are other than hydrogen.

23. A method of treating a disease caused by hyperactivity of an excitatory amino acid which comprises administering an effective amount of a compound of claim 18.

24. The method of claim 23, wherein the disease is a neurological or psychiatric disorder triggered by overstimulation of the AMPA receptor.

* * * * *